(12) United States Patent
Borodulin et al.

(10) Patent No.: US 6,712,761 B2
(45) Date of Patent: Mar. 30, 2004

(54) COMBINATION OF A VAGINAL SPECULUM WITH A SINGLE-LENS COLPOSCOPE

(76) Inventors: German Borodulin, 583 46th Ave., San Francisco, CA (US) 94121; Ananias Diokno, 480 Hillspur Rd., Ann Arbor, MI (US) 48105; Alexander Shkolnik, 485 Dartmouth Ave., San Carlos, CA (US) 94070

( * ) Notice: Subject to any disclaimer, the term of this patent is extended or adjusted under 35 U.S.C. 154(b) by 71 days.

(21) Appl. No.: 10/161,590

(22) Filed: Jun. 4, 2002

(65) Prior Publication Data

US 2003/0225313 A1 Dec. 4, 2003

(51) Int. Cl.7 .................................................. A61B 1/00
(52) U.S. Cl. ........................ 600/184; 600/220; 600/221
(58) Field of Search ................................. 600/184, 188, 600/190, 193, 196, 201, 210, 214, 215, 219, 220, 221, 222, 223, 246, 175, 176, 183, 200

(56) References Cited

U.S. PATENT DOCUMENTS

| | | | | |
|---|---|---|---|---|
| 2,844,144 A | * | 7/1958 | Massey | 600/121 |
| 4,210,133 A | | 7/1980 | Castaneda | |
| 4,905,670 A | * | 3/1990 | Adair | 600/104 |
| 5,251,613 A | | 10/1993 | Adair | |
| 5,479,293 A | | 12/1995 | Reed | |

OTHER PUBLICATIONS

"Bulletin of the World Health Organization" 2000, V. 78(8), pp. 964–967.

* cited by examiner

Primary Examiner—Beverly M. Flanagan

(57) ABSTRACT

The invention relates to a combination of a vaginal speculum with a single-lens colposcope for use in a screening process for detecting mucosal abnormalities of cervical intraepithelial neoplasia or invasive cancer, e.g., in the vaginal cavity or on the external parts of the genitalia, as an addition to a Pap Smear screening process. The vaginal speculum is identical to a conventional speculum in its shape, dimensions, and function and differs from a conventional instrument only by having on the inner surface of the lower blade a small projection with a slot for guiding a single-loop colposcope. The latter consists of a tubular rod that can be slidingly inserted into the aforementioned slot and support on its distal end an optical lens. The lens may have a central opening for insertion of surgical instruments, e.g., a biopsy sampler. The proximal end of the tubular rod may support a rubber bulb for suction fluids from the distal end of the lower blade via the tubular rod. In use, the colposcope is inserted into the vaginal speculum through the guide slot so that the physician can manipulate with the colposcope by moving it in axial direction for focusing the lens and by turning the rod to the left or to the right for observing an area of interest. The vaginal speculum and the colposcope can be molded from plastic and can be disposable.

16 Claims, 3 Drawing Sheets

COMBINATION OF A VAGINAL SPECULUM WITH A SINGLE-LENS COLPOSCOPE

FIELD OF THE INVENTION

The present invention relates to the field of medical devices for conducing close range physical medical examinations, in particular to colposcopes used for conducting gynecological and urological examinations.

BACKGROUND OF THE INVENTION

Two methods are used for earlier detection of cervical cancer and pre-cancer: cytology and colposcopy. Cytology is a screening method that is practical and economical, while colposcopy is a diagnostic method for clinical diagnosis of patients with abnormal cytology. Each method has its practical limitations and strength in cancer detection, and both methods complement each other.

Currently a standard gynecological exam comprises the use of a speculum, visual examination of the vaginal interior cavity and related structures without any use of magnification, pulpation of the pelvic region and a Pap smear. If the abnormalities are not detected visually, they may be detected by the Pap smear or Pap test. The word "Pap" is short for Papanicolaou, which is the last name of the doctor who studied earlier detection of changing cervical cells. When conducting Pap smear screenings, the gynecologist gently scrapes and collects exfoliated cells from the surface of the cervix by a thin wooden stick and a tiny brush and places them on slides that are sent to a cytologist for further examination.

In spite of its cancer detection shortcomings, Pap Smear screening is generally recognized as a practical and economical procedure for the early detection of cervical cancer.

However, there has been an increasing amount of controversy surrounding the Pap smear, regarding the quality of the sampling taken and consequently the accuracy of the results. The false negative rate for Pap smears (indicating nothing wrong, when there is a problem) has been shown to be approximately 30%.

In the early stages of cervical disease, abnormal cell exfoliation is slow and most abnormal cells are located below the surface or are trapped by a keratin barriers covering the cervical surface. In these circumstances, the Pap Smear screening process is a relatively insensitive indicator of cervical health due to inaccessibility of abnormal cells that are otherwise indicators of cancerous or pre-cancerous tissue.

If abnormalities (such as dysplasia, i.e., pre-cancerous cells, also called cervical intraepithelial neoplasia or low high-grade squamous intraepithelial lesion, etc.) are detected by Pap test, the patient is brought in a second time for a more detailed examination using a colposcope.

While the Pap Smear process is designed for initial screening, colposcopy and related procedures are generally used to confirm Pap Smear abnormalities and to grade cancerous lesions.

A colposcopy is the viewing of the cervix, vagina, and vulva through a high-powered microscope called a colposcope. The colposcope consists of a pair of binoculars attached to a stand and an illuminating unit. Direct examination through the colposcope allows the detection of abnormalities on the cervix that can not be seen with the naked eye. This procedure is performed with a vaginal speculum, which is used to hold open the vaginal cavity in order to allow viewing of the cervix. The cervix and vagina are swabbed with a diluted acetic acid (vinegar). The solution highlights areas (tissue which is thickened, such as cancer cells) by turning them white (instead of a normal pink color). Abnormal areas can also be identified by looking for a characteristic pattern made by abnormal blood vessels, which may indicate new growth, such as cancer.

If any abnormal areas are seen, the doctor will take a biopsy of the tissue. In a biopsy, a tiny sample of tissue will be removed from the area with a tweezer-like instrument. An endocervical scraping from the os (the opening in the middle of the cervix) may be taken as this is the area where often abnormal cells begin.

The effectiveness of this colposcopy procedure, which is a subjective visual assessment in detecting abnormalities, is believed to be approximately 85%, and this effectiveness is due in part to the greater amount of experience which physicians, who utilize this procedure, generally have. It should be noted, however, that the colposcope is difficult to use because of its complexity. Furthermore, it is not available in all medical facilities. It is also expensive and not at all portable.

Because colposcopy is a specialized procedure, requiring advanced and comprehensive training on a complicated and expensive apparatus, colposcopy is typically only performed on patients who have had an abnormal screening procedure (i.e., Pap smears or if the cervix looks abnormal during a routine naked eye examination).

It is well known that during routine gynecological examination it is impossible to diagnose diseases or other problems simply by looking at the cervix with the naked eye. A magnified view is necessary to find any abnormalities, or to show that cervical changes are not a cause for concern.

Therefore, the need for a portable magnification apparatus useful as a colposcope is present. Many attempts have been made heretofore to develop a portable colposcopic apparatus that would allow for the ready use of the colposcope as a screening tool, thereby increasing the opportunity for diagnosis and treatment.

U.S. Pat. No. 4,210,133 issued in 1980 to J. Castaneda discloses a vaginal colposcope for examination through the throat of the womb including a guide-tube and a microscope. The guide-tube is adjustably attached to a vaginal speculum and has its own illumination system, a graduated collar for focusing the microscope, and fine-adjustment clamps for preventing the accidental movements of the microscope. The microscope is adjustably positioned in the guide-tube so that it can focus on a plurality of microscopic fields without movement of the guide-tube. It has two illumination systems, one providing light for vision, the other an electronic flash for a photographic camera. The microscope can be removed from the stationary guide-tube, its objectives and oculars replaced by elements with different powers, and reinserted in the guide-tube to provide examination at variable magnifications.

This device is expensive, complicated in construction, and occupies the entire cavity of the speculum so that it cannot be used, e.g., for taking a biopsy during the observation.

U.S. Pat. No. 5,251,613 issued in 1993 to E. Adair discloses a tubular optical cervical colposcope (videoscope) insertable into a vaginal speculum for examining the cervix and vagina for cancerous lesions or other abnormalities. Although this instrument leaves some space for simultaneous use of other instruments such as a laser electrode, this videoscope is a complicated and expensive device, which is connected to a videochromator, video-control unit, light source, monitor, etc. The device requires expertise for using the instrument.

U.S. Pat. No. 5,479,293 issued in 1995 to T. Reed discloses a portable apparatus useful for close range physical examinations, in particular for use as a colposcope. The portable apparatus includes a stereoscopic optical unit, a main frame lens holder, an auxiliary frame lens holder, a light and mount therefor, a filter and mount therefor, and a support structure which allows the component parts to be maintained in precise optical alignment and allows the apparatus to be worn by a user in the manner of eyeglasses. These components are constructed and arranged to provide for an undistorted short focal length and magnification as necessary for clear close range visualization of body tissue.

A disadvantage inherent in the device of U.S. Pat. No. 5,479,293 and in all spectacle-like colposcopes consists in that this device is rather expensive, complicated in construction, and allows for observation of the zone of interest only at a distance.

Meanwhile, the use of a simplified one-lens colposcope may be extremely useful for preliminary screening of cervical cancer or other abnormalities. This was confirmed by the study described by Adtya Parasharu, et al. in "Bulletin of the World Health Organization", 2000, V. 78 (8), pp. 964–967. The colposcopy was conducted with the use of a one-lens hand-held instrument consisting of a lens supported by a handle and an illumination device located under the lens. This inexpensive device was used for detecting precancerous lesions of the uterine cervix. The instrument, which is called "Magnivisualizer", improved the detection rate of early cancerous lesions from 60%, for unaided visual inspection, to 95%. It is also permitted detection of 58% of cases of flow-grade dysplasia and 83% of cases of high-grade dysplasia. None of these cases were detectable by unaided visual inspection.

Although this device is not very expensive, it suffers the same disadvantages as the aforementioned spectacle-like colposcopes, i.e., the device cannot be inserted into a speculum and therefore cannot be used for observation of the zone of interest from a close distance.

The need, therefore, for a portable inexpensive magnification apparatus useful as a colposcope is present.

OBJECTS OF THE INVENTION

A primary object of the present invention is to provide a portable apparatus suitable for close range visual medical examinations at undistorted short focal lengths. It is another object of the present invention to provide a combination of a vaginal speculum with a single-lens colposcope for visual lens-aided detection of abnormal cells that may be indicators of cancerous or pre-cancerous tissue. It is another object to provide the aforementioned colposcope, which is simple in construction and inexpensive to manufacture. Still another object is to provide a conventional vaginal speculum with means for insertion and guiding of the aforementioned colposcope without violation of the speculum's functions. Another object is to provide the aforementioned colposcope which is disposable. A further object is to provide the aforementioned colposcope with means for removing a liquid discharge from the speculum. Still another object is to provide a single-lens colposcope with means for insertion of rod-like tools into the vaginal speculum through the lens without obscuring the field of view through the lens.

SUMMARY OF THE INVENTION

The invention relates to a combination of vaginal speculum with a single-lens colposcope for use in a screening process for detecting mucosal abnormalities of cervical intraepithelial neoplasia or invasive cancer, e.g., in the vaginal cavity or on the external parts of the genitalia, as an addition to a Pap Smear screening process. The vaginal speculum is identical to a conventional speculum in its shape, dimensions, and function and differs from a conventional instrument only by having on the inner surface of the lower blade a small projection with a slot for guiding a single-loop colposcope. The latter consists of a tubular rod that can be slidingly inserted into the aforementioned slot and supports on its distal end an optical lens. The lens may have a central opening for insertion of surgical instruments, e.g., a biopsy sampler. The proximal end of the tubular rod may support a rubber bulb for suction of fluids from the distal end of the lower blade via the tubular rod. In use, the colposcope is inserted into the vaginal speculum through the guide slot so that the physician can manipulate with the colposcope by moving it in the axial direction for focusing the lens and by turning the rod to the left or to the right for observing an area of interest. The vaginal speculum and the colposcope can be molded from plastic and can be disposable.

DETAILED DESCRIPTION OF THE INVENTION

Figure 1:
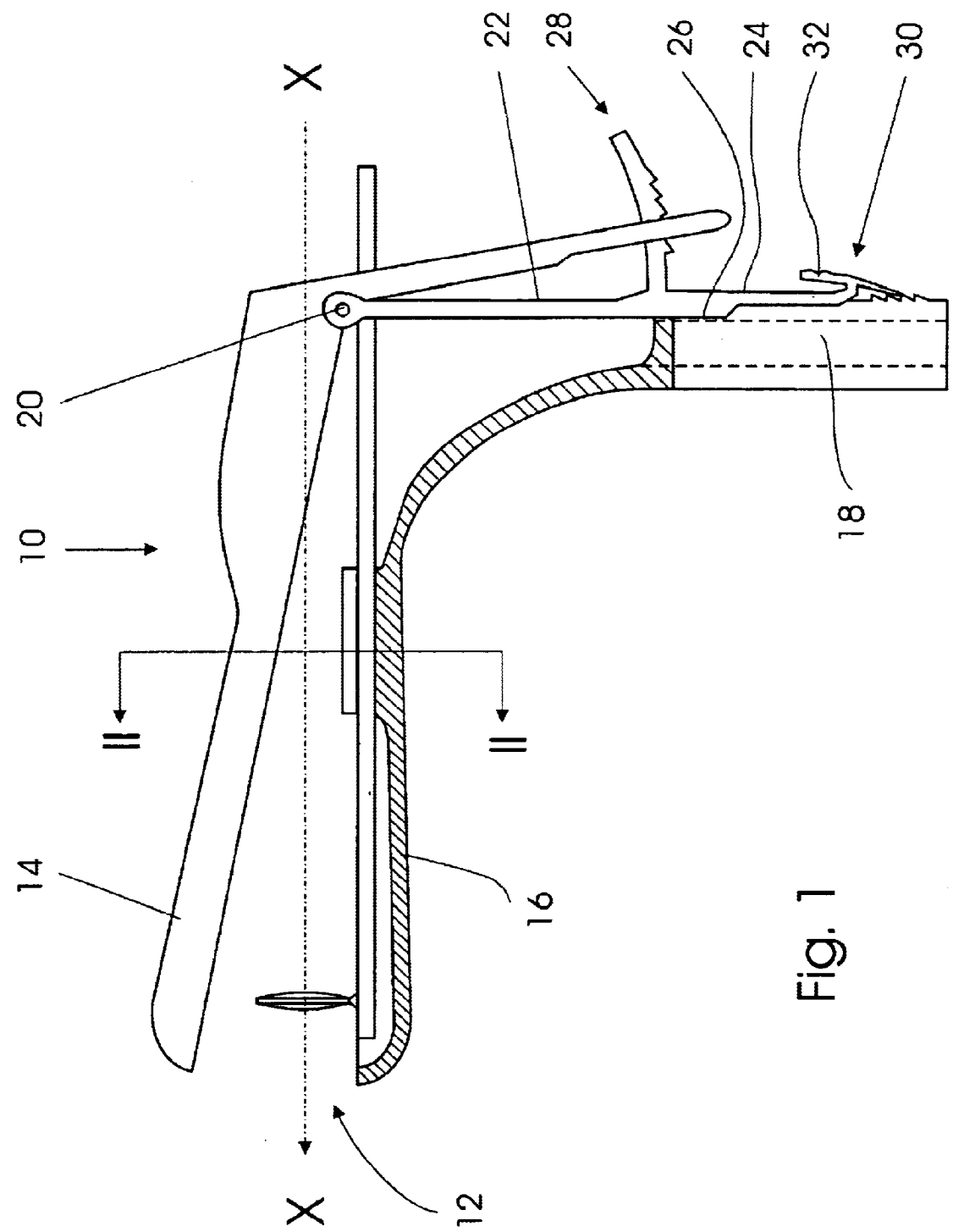
FIG. 1 is a general side view of a vaginal speculum of the invention in an open state with a single-lens colposcope inserted into the speculum.

FIG. 1 is a general side view of a vaginal speculum 10 of the invention in an open state with a single-lens colposcope 12 inserted into the speculum 10. More specifically, the single-lens colposcope 12 can be used in conjunction with a vaginal speculum of any type that consists in general of two blades insertable into the vagina for spreading and expanding the vagina in a radial direction for observing the conditions of the vaginal walls, for fulfilling treatment procedures, or for conducting appropriate measurements, e.g., for determining positions and severity of vaginal prolapses. In the embodiment shown in FIG. 1, the vaginal speculum consists of a moveable blade 14 pivotally connected to an L-shaped stationary blade 16 having a handle portion 18 arranged substantially perpendicular to the stationary blade 16. Pivotal connection between the blades 14 and 16 is carried out through the intermediary of pivotal axles or pins, only one of which 20 is shown in FIG. 1, since the other one is on the opposite side of the blade not seen in FIG. 1. The pins 20 are rigidly connected to or formed integrally with a fork-like portion 22 on the upper end of a slider 24 slidingly installed in a guide slot (not shown) formed on the rear surface 26 of the handle portion 18.

As a conventional vaginal speculum of the aforementioned type, the speculum 10 of FIG. 1 has on its proximal side a ratchet-type blade rotating mechanism 28 and an upper blade raising mechanism 30 with a ratchet teeth-and-pawl lock device 32.

Since the vaginal speculum suitable for use in conjunction with the single-lens colposcope of the invention can be of any type with a couple of parallel blades moveable apart by pivotal rotation or by parallel displacements in the transverse direction, the speculum does not require detailed description. The vaginal speculum 10 illustrated in FIG. 1 is the device described in U.S. Pat. No. 3,716,047 issued in 1970 to W. Moore et al., which is incorporated herein by reference. Other vaginal specula suitable for the purposes of the present invention are described in the following U.S. Pat. No. 2,579,849 issued in 1951 to L. Newman; U.S. Pat. No. 3,747,591 issued in 1973 to B. Golden; U.S. Pat. No. 3,815,585 issued in 1974 to J. Fiore; U.S. Pat. No. 6,048,308 issued in 2000 to J. Strong; etc.

Figure 2:
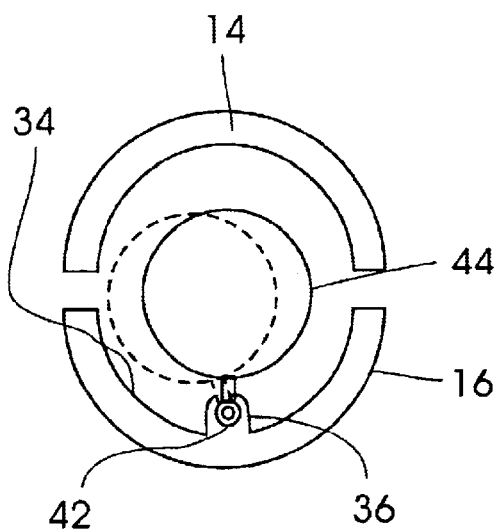
FIG. 2 is a sectional view of the device of the invention along line II—II of FIG. 1.
Figure 3:
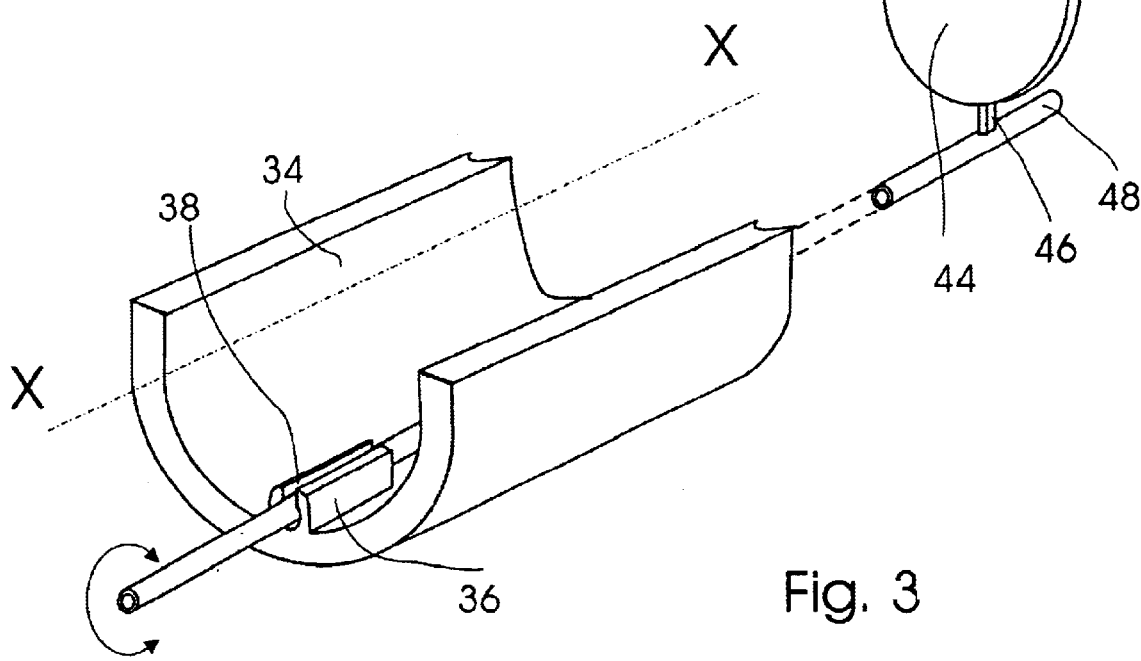
FIG. 3 is a three-dimensional view of a part of the speculum illustrating a colposcope guiding and retaining mechanism.

FIG. 2 is a sectional view of the device of the invention along line II—II of FIG. 1, and FIG. 3 is a three-dimensional view of a part of speculum illustrating a colposcope guiding and retaining mechanism formed in the vaginal speculum 10. As can be seen from FIGS. 2 and 3, the inner surface of 34 of the stationary blade 16 has a small radial projection 36 with a narrow radial slot 38 extending through the projection 36 in the longitudinal direction of the blades shown by the axis X—X in FIGS. 1 and 3.

Reference numeral 40 designates a single-lens colposcope, which consists of a tubular rod 42 and a magnifying glass or lens 44 attached to the distal end of the rod 42 by means of a radial arm 46 extending in a radial direction from the end of the rod 42. As shown in FIG. 2, the rod 42 may have a diameter greater than the width of the slot 38, while the radial arm 46 should have a width equal to or smaller than the width of the slot 38. It is also understood that the height of the radial arm 46 is greater than the depth of the slot 38 in the projecting portion 36 so that the colposcope 40 could be inserted into the lower blade 34 through the projection 36. If necessary, the rod 42 may have the diameter equal to the width of the slot 38. The lens 44 may be permanently or removably attached to the rod 42 at a small distance from the tip 48. The entire single-lens colposcope 40 can be molded as an integral unit from a plastic and may be disposable. If necessary, the colposcope may be assembled from a rod and a lens and be suitable for cleaning and multiple use.

Figure 4:
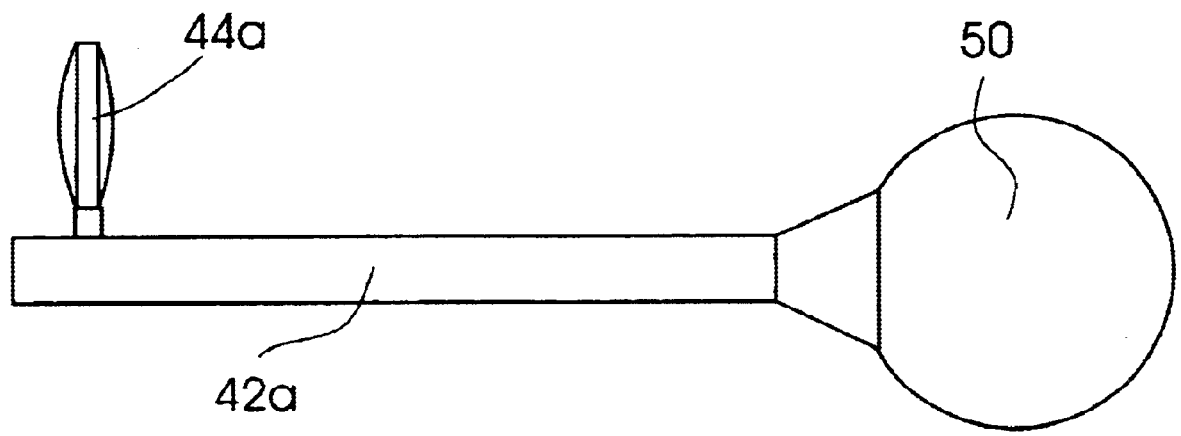
FIG. 4 is a view of a single-lens colposcope of another embodiment with a suction rubber bulb attached to the end of the tubular rod opposite to the lens.

As shown in FIG. 4, which is a view of a single-lens colposcope of another embodiment, a suction rubber bulb 50 can be attached to the end of the tubular rod 42a opposite to the lens 44a.

Figure 5:
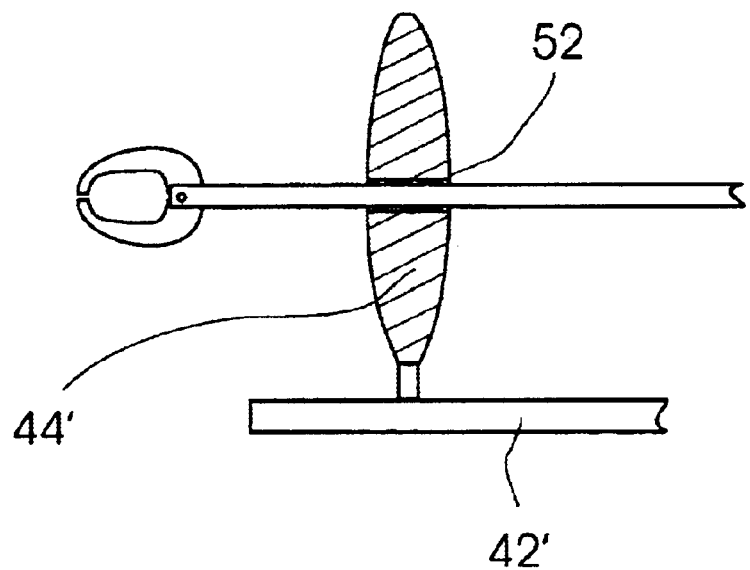
FIG. 5 is a side sectional view of a part of a colposcope with a central opening in the lens for passing elongated surgical instruments through the lens.

In the embodiment of FIG. 5, which is a side sectional view of a part of the colposcope with a rod 42' supporting a lens 44'. It can bee seen that the lens 44' may have a small opening 52, e.g., in the center of the lens. This opening will not prevent the viewer from observation of the zone of interest through the lens 44', but at the same time will allow insertion of thin rod-like tools such as an instrument 54 for taking a sample of a tissue for biopsy.

In use, first the speculum 10 is utilized for its specific purpose, e.g., for examination of conditions on the vaginal wall and for checking the presence or absence of pelvic organ prolapses. The blades 14 and 16 are inserted into the patient's vagina in their closed state and then are moved apart for dilation of the vaginal canal in a conventional manner by adjusting the position of the upper blade 14 with respect to the lower blade with the use of the mechanism 32 and by pushing on the lever of the blade rotating mechanism 28.

The single-lens colposcope 40 is then inserted into the speculum 10, e.g., for visual lens-aided detection of abnormal cells that may be indicators of cancerous or precancerous tissue. More specifically, the distal tip 48 (FIG. 3) of the rod 42 is inserted into the projecting portion 36 from the proximal end of the colposcope 40 by aligning the radial arm 46 with the position of the slot 38 and by pushing the rod 42 forward with the passage of the radial projection 46 through the slot 38.

The lens 44 can be moved back and forth in the direction of axis X—X (FIG. 1 and FIG. 3) by moving the colposcope manually with the use of the proximal end that projects from the speculum 10 for manually focusing the lens 44 with respect to the area of observation or can be turned to the left or right as shown in FIG. 2. If necessary, additional manipulation of the lens 44 can be carried out by slightly moving the speculum itself together with the colposcope 40 inserted into the speculum.

In the case of the embodiment of the invention with the lens 44' that has a central opening 52 shown in FIG. 5, the aforementioned opening can be used, without obscuring the field of view through the lens 44', for insertion of thin rod-like instruments such as a biopsy sampling tool 54, or a laser electrode (not shown). The biopsy sampling or ablation with the laser electrode can be carried out by observing the operation site under magnification through the lens 41. In the case of the embodiment of the colposcope with the suction bulb 50 on the proximal end of the tubular rod 42a shown in FIG. 4, the smoke, products of burned tissue formed during the use of a laser, or other gaseous or liquid substances accumulated in the lower blade of the speculum in front of the distal end 48 of the tubular rod 42a can be removed from the speculum through the tubular rod 42a by means of the suction bulb 50.

Thus, the portable colposcopic apparatus of the invention can be used as an effective screening tool, which will increase the opportunity for diagnosis and treatment.

In other words, it has been shown that the invention provides a portable apparatus suitable for close range visual medical examinations of conditions in the vaginal cavity at undistorted short focal lengths. The invention provides a combination of a vaginal speculum with a single-lens colposcope for visual lens-aided detection of abnormal cells that may be indicators of cancerous or precancerous tissue. The colposcope of the invention is simple in construction and inexpensive to manufacture. In another aspect, the invention provides a conventional vaginal speculum with means for insertion and guiding of the aforementioned colposcope without violation of the speculum's functions. The colposcope can be disposable and provided with means for removing a gaseous or liquid discharge from the speculum. The lens of the colposcope may have a central opening for insertion of thin rod-like tools such as a biopsy sampling tool or a laser electrode that can be used without obscuring the field of view through the lens.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, a vaginal speculum may have a design different from the one shown in the drawings, e.g., it may be the speculum with removable blades disclosed in our pending U.S. patent application Ser. No. 09/565,613 filed on May 4, 2000. The lenses can be replaceable and detachable from the radial projection on the distal end of the rod for installation of lenses with different focal distances. The colposcope can be inserted into the upper blade, or used individually without the speculum or in conjunction with other instruments insertable into a human body. In combination with illumination light the lens may increase brightness of the area of observation. The lens can be inclined with respect to the rod. The colposcope can be reusable with a metal tubular rod and a glass lens.

What is claimed is:

1. A combination of a vaginal speculum with a single-lens colposcope comprising:

a vaginal speculum having a first blade with a distal end and a proximal end and a second blade with a distal end and a proximal end, said blades having means on their respective proximal ends for moveably interconnecting said proximal ends of said first blade and of said second blade for possibility of relative movement between said first blade and said second blade, said first blade having an inner surface and said second blade having an inner surface, said inner surface at least of said second blade having a colposcope guiding means; and a single-lens colposcope comprising an elongated means moveably insertable into said colposcope guiding means and having a distal end and a proximal end;

an optical lens attached to said distal end of said elongated means; and connection means for connecting said optical lens to said distal end of said elongated means, said connection means having dimensions that allow passing of said connection means through said colposcope guiding means;

said vaginal speculum having a longitudinal direction, said colposcope guiding means comprising a radial inward protrusion formed on said inner surface at least of said second blade with a slot passing through said protrusion in said longitudinal direction, said slot having a width and a depth, said connection means comprising a radial projection extending radially from said distal end of said elongated means, said radial projection having a height and a width, said height of said radial projection being greater than said depth of said slot, and said width of said radial projection being smaller than said width of said slot.

2. The combination of claim 1, wherein said elongated means comprises a rod.

3. The combination of claim 2, wherein said rod is a tubular rod.

4. The combination of claim 3, wherein said tubular rod has suction means attached to said proximal end of said tubular rod for suction of fluid substances from said speculum through said proximal end of said tubular rod.

5. The combination of claim 4, wherein said suction means is a flexible bulb.

6. The combination of claim 1, wherein said optical lens has a central opening for insertion of elongated tools through said optical lens.

7. The combination of claim 6, wherein said elongated means comprises a rod.

8. The combination of claim 7, wherein said rod is a tubular rod.

9. The combination of claim 8, wherein said tubular rod has a suction means attached to said proximal end of said tubular rod for suction of fluid substances from said speculum through said distal end of said tubular rod.

10. The combination of claim 8, wherein said suction means is a flexible bulb.

11. The combination of claim 1, wherein said vaginal speculum is a made of a plastic and is a disposable vaginal speculum.

12. The combination of claim 11, wherein said single-lens colposcope is made of a plastic and is a disposable single-lens colposcope.

13. The combination of claim 12, wherein said elongated means comprises a rod.

14. The combination of claim 13, wherein said rod is a tubular rod.

15. The combination of claim 14, wherein said tubular rod has a suction means attached to said proximal end of said tubular rod for suction of fluid substances from said speculum through said proximal end of said tubular rod.

16. The combination of claim 15 wherein said suction means is a flexible bulb.

* * * * *